United States Patent
Weidman

(10) Patent No.: US 7,743,876 B2
(45) Date of Patent: Jun. 29, 2010

(54) STETHOSCOPE SHIELD SYSTEM AND METHOD OF SHIELDING STETHOSCOPE USING THE SAME

(75) Inventor: Richard C. Weidman, 9505 Neuse Way, Great Falls, VA (US) 22066

(73) Assignee: Richard C. Weidman, Great Falls, VA (US)

( * ) Notice: Subject to any disclaimer, the term of this patent is extended or adjusted under 35 U.S.C. 154(b) by 34 days.

(21) Appl. No.: 11/952,356

(22) Filed: Dec. 7, 2007

(65) Prior Publication Data

US 2008/0230303 A1    Sep. 25, 2008

Related U.S. Application Data

(60) Provisional application No. 60/873,401, filed on Dec. 7, 2006.

(51) Int. Cl.
  *A61B 7/02*    (2006.01)
  *B32B 33/00*   (2006.01)
(52) U.S. Cl. .................... 181/131; 428/42.3; 428/41.9; 428/42.2; 428/42.1
(58) Field of Classification Search ............... 181/131; 604/387; 428/42.3, 41.9, 42.1, 42.2
See application file for complete search history.

(56) References Cited

U.S. PATENT DOCUMENTS

| | | | |
|---|---|---|---|
| 4,714,276 A * | 12/1987 | Greig | ........................ 283/63.1 |
| 4,867,268 A | 9/1989 | Ulert | |
| 4,871,046 A | 10/1989 | Turner | |
| 5,286,546 A * | 2/1994 | Su | ............................. 428/194 |
| 5,424,495 A | 6/1995 | Wurzburger | |
| 5,448,025 A | 9/1995 | Stark et al. | |
| 5,528,004 A | 6/1996 | Wurzburger | |
| 5,587,561 A | 12/1996 | Budayr et al. | |
| 5,641,550 A * | 6/1997 | Berman et al. | ............. 428/40.9 |
| 5,686,706 A | 11/1997 | Wurzburger | |
| 5,808,244 A | 9/1998 | Knight et al. | |

(Continued)

OTHER PUBLICATIONS

M.A. Smith et al., "Contaminated Stethoscopes Revisited", Arch Intern Med/vol. 156, Jan. 8, 1996, pp. 82-84.

(Continued)

*Primary Examiner*—Jeffrey Donels
*Assistant Examiner*—Forrest M Phillips
(74) *Attorney, Agent, or Firm*—Studebaker & Brackett PC; Donald R. Studebaker

(57) ABSTRACT

A stethoscope shield system and method of preventing contamination of an instrument, particularly a stethoscope, includes a plurality of substantially planar shields stacked one upon the other, each of the shields having a substantially identical outer periphery and including a first surface and a second surface such that adjacent shields are attracted to one another with the first surface of each of these shields in contact with the second surface of an adjacent shield with a first shield of the plurality of shields being in contact with the diaphragm of the stethoscope for supporting the stacked shields, wherein the attraction force between the stacked shields occurs over less than an entire surface of at least one of the first and second surfaces and the attraction between the stacked shields has at least one of a consecutively increasing attraction area and a consecutively increasing attraction strength, and an exposed shield of the stacked shields is removed after contacting the body of a patient.

33 Claims, 2 Drawing Sheets

U.S. PATENT DOCUMENTS

| | | | |
|---|---|---|---|
| 5,949,032 A | 9/1999 | Wurzburger | |
| 6,009,971 A | 1/2000 | Weidman et al. | |
| 6,458,442 B1 * | 10/2002 | McKay | 428/40.1 |
| 6,777,055 B2 * | 8/2004 | Janssen et al. | 428/41.8 |
| 6,794,002 B2 * | 9/2004 | Shinbo | 428/40.1 |
| 6,958,179 B2 * | 10/2005 | Carlson et al. | 428/40.1 |
| 7,413,786 B2 * | 8/2008 | Wada et al. | 428/40.1 |
| 2001/0023001 A1 | 9/2001 | Weiss et al. | |
| 2003/0005934 A1 * | 1/2003 | Japuntich et al. | 128/206.15 |

OTHER PUBLICATIONS

MA Marinella et al., "The Stethoscope a Potential Source of Nosocomial Infection", Arch Intern Med/vol. 157, Apr. 14, 1997, pp. 786-790.

"Graham-Field To Distribute Patented Stethoscope Cover: Scope Shield Protects Patients Against Infectious Diseases" Graham-Field Health Products, Inc., Feb. 18, 1998.

International Search Report; PCT/US2007/086765; May 13, 2008.

* cited by examiner

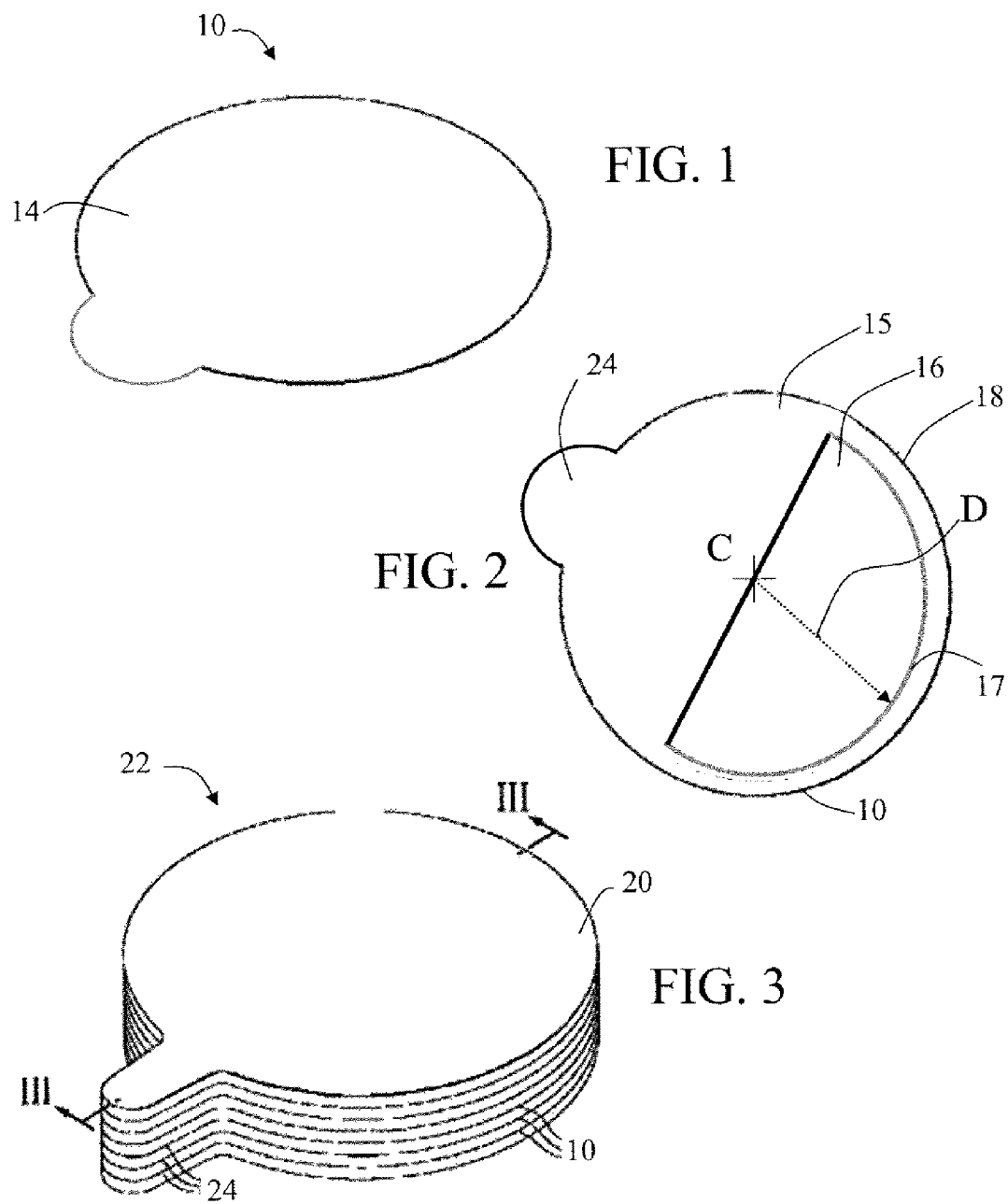

STETHOSCOPE SHIELD SYSTEM AND METHOD OF SHIELDING STETHOSCOPE USING THE SAME

TECHNICAL FIELD OF THE INVENTION

The present invention is directed to a stethoscope shielding system and a method of shielding a stethoscope using a stethoscope shield system which attaches to the stethoscope head prior to initial use such that an outermost shield is individually removed to prevent simultaneous removal of multiple innermost shields when the single outermost shield is removed.

BACKGROUND OF THE INVENTION

Multi-layered shields covering stethoscopes (and other instruments), as described in U.S. Pat. No. 6,009,971, must be individually removable, from the outermost shield down to the innermost shield nearest to the diaphragm of the stethoscope. This may be difficult to achieve in that pulling on the outermost shield to remove it may inadvertently cause the removal simultaneously of one or more shields lying between the outermost shield and the diaphragm of the stethoscope. The method described herein shows how to construct and use multi-layered stethoscope shields to avoid this problem and to ensure that the shields can be individually removed (and discarded) in sequence from the outermost shield down to the last shield nearest to the stethoscope diaphragm. Also disclosed is a structure of a plurality of shields which is suitable for such individual removal.

SUMMARY OF THE INVENTION

The primary object of the present invention to overcome the aforementioned shortcomings associated with the prior art shields and dispensing methods.

Yet another object of the present invention is to provide a stethoscope shield system that allows for individual removal of outermost shields to reduce waste.

Yet another object of the present invention is to provide a method for preventing contamination of an instrument by use of individually removed protective shields.

BRIEF DESCRIPTION OF THE DRAWINGS

FIG. 1 is a perspective view of an individual shield for protecting a patient from the transmission of contaminants from an instrument, particularly a stethoscope in accordance with the present invention.

FIG. 2 is a plan view of an exemplary shield in accordance with the present invention.

FIG. 3 is a perspective view of an exemplary stethoscope shield system for application to a head of a stethoscope in accordance with the present invention.

DETAILED DESCRIPTION OF THE PRESENT INVENTION

Figure 4:
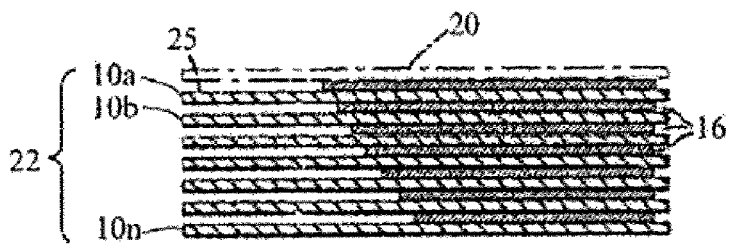
FIG. 4 is a cross-sectional view of the stethoscope shield system along line III-III of FIG. 3 in accordance with the present invention.

Reference will now be made to the several figures in which the various elements of the present invention will be discussed in detail. Like reference numerals will be utilized to designate like elements throughout the several figures.

With reference now to FIG. 1, there is shown a protective shield 10 for application to an instrument and particularly, application to the head of a stethoscope. The shield 10 includes a generally planar piece of sound transmissive material 14 wherein the sound transmissive material 14 may be of a variety of substances. However, it is preferred that the sound transmissive material 14 be of a thin sheet of plastic or paper or some other material which will not interfere with the transfer of sound between the patient and the diaphragm of the stethoscope. It is known that paper and plastic are commonly used materials in the health care profession and are advantageous in that they are both inexpensive and inherently disposable. In order to prevent body fluids from penetrating the shield 10, a shield made of paper would most likely include a thin fluid impermeable coating such as plastic or wax. In accordance with a preferred embodiment of the present invention, a thin essentially disc-shaped shield forms a waterproof and impermeable barrier to microorganisms for the stethoscope. As noted hereinabove, each of the disc-shaped shields 10 are disposable and are preferably constructed of a plastic polymeric material, such as polyester and/or polyethylene having a thickness in the range of about 0.01 mils to about 4.0 mils, and preferably about 0.5 mils thick. The thickness of the shields 10 must provide for acoustic transmission and still be structurally stiff enough to resist permanent physical deformation due to removal of the shields 10. However, with the advent of electronic stethoscopes and electronic instruments, shields of different thicknesses are contemplated. According to the present invention, the preferred thickness of the shields 10 are based upon acoustic stethoscopes, but other shield thicknesses are possible based upon the sensitivities of future designs of stethoscopes, as well as other instruments used in the healthcare industry for monitoring patients' physical status. Moreover, using a stack of shields 10 having differing thicknesses attached to a stethoscope may be used for maintaining structural integrity of the stacked shields, and at the same time providing accurate acoustic transmission.

As can be seen from FIG. 2, a first surface or underlying surface 15 of the shield 10 includes an adhesive pad 16 which allows each sequential shield 10 to be adhered to one another, as well as an initial shield to be adhered to a surface of the stethoscope. This adhesive pad 16 is preferably provided in the form of a substantially semicircular pad having a diameter D defining an outer circumference 17 adjacent a periphery 18 of the shield 10. Although the outer circumference 17 of the adhesive pad 16 is shown to be spaced from the periphery 18 of the shield 10, the diameter D of the adhesive pad 16 may extend out to the periphery 18 of the shield 10. The adhesive pad 16 utilized in accordance with the present invention is a removable adhesive material, such as that used in note pads sold by 3M Corporation under the trademark "POST-IT NOTE". As such, the adhesive pad 16 will releasably hold a plurality of shields 10 to one another as a stethoscope shield system, as well as releasably hold the stethoscope shield system to a surface of the stethoscope. Alternatively, the adhesive pad 16 may be formed as a strip of adhesive material extending along a direction perpendicular to the extending direction of a tab 24 of the shield 10.

The adhesive pads 16 may be formed for a "break-away" adhesive between adjacent shields 10. For example, the adhesive pad 16 may include a multilayered structure having upper and lower adhesive layers, which both have opposing adhesive surfaces, i.e., double-sided adhesive layers, with a non-adhesive layer disposed between the upper and lower adhesive layers. Thus, when the multilayered adhesive pad is disposed between adjacent shields 10, removal of a used shield 10 from an underlying unused shield 10 results in removal of the upper adhesive layer. The unused shield 10 now retains the non-adhesive layer and underlying lower adhesive layer. However, the user will only actually see the non-adhesive layer.

As can be seen from FIG. 3, a stethoscope shield system 22 may include a stack of a plurality of shields 10 having the adhesive 16 disposed therebetween. While FIGS. 3 and 4 show shields 10 stacked one upon the other, the actual number of shields 10 forming the system 22 which is applied to the stethoscope may vary and is clearly dependent upon the thickness and sound transmissibility of the material forming the shield 10 and the adhesive pad 16. For example, the thicker the materials for forming the shields 10 and the adhesive pad 16, the fewer number of shields 10 are provided in the stack in order to ensure that the physician (or healthcare provider) can adequately hear the sounds of the body during an exam. For this reason, the thickness of the adhesive pad 16 is kept to a minimum.

In FIGS. 3 and 4, the system 22 includes the plurality of shields 10 stacked one upon the other and includes a release liner 20. This release liner 20 is removed from an uppermost shield 25 prior to application to the stethoscope, the process of which will be described in greater detail hereinbelow. The release liner 20 acts to preserve the integrity of the adhesive pad 16 disposed upon an uppermost shield 10 and aids in preventing contamination of the system 22. Preferably, the system 22 is provided individually within a sealed pouch, or provided as multiple systems 22 within a box, which maintains the integrity of the system(s) 22 when being handled. When used, the system 22 is removed from a clean container, either individually wrapped or from a disposable box, and the release liner 20 is removed so as to expose the adhesive pad 16 disposed upon the uppermost shield 25 for application to a stethoscope. The adhesive pad 16 disposed adjacent to the release liner 20 will have at least one of the greatest bonding strength and/or the greatest adhesive bonding area for attachment to the stethoscope, whereas the subsequent adhesive pads 16 disposed between adjacent shields 10 will have lower bonding strengths and/or adhesive bonding areas. In addition, the uppermost shield 25, which is applied to the stethoscope, may have a fenestrated structure to clearly indicate to the user that the system 22 needs to be replaced. The fenestrated structure would not be provided to function as a shield, but rather an end-of-use indicator to the user. Alternatively, the uppermost shield 25 may be used as a shield and simply have a physical marking to indicate to the user that replacement of the system 22 is required.

It is to be noted that the foregoing and following descriptions are directed toward the use of a plurality of shields stacked one upon another in connection with a stethoscope. However, this concept is likewise applicable to any instrument wherein the need for maintaining a contaminant free surface is present. It should also be noted that each of the shields 10 includes the tab 24 that extends from the periphery 18 of the shield 10 to facilitate removal of underlying shields 10. For example, if the user desires to remove several shields at one time, then the user may select the group of shields 10 to be removed and pull on the tab of the desired bottommost shield. Moreover, the tab 24 may have different geometries so long as the tab 24 provides a visual indication to the user an orientation of the adhesive pads 16. For example, a simple marking on the shield 10 may provide the user with an indication as to the areas of the shields 10 that are lacking the adhesive pads 16 and from which direction removal of the used shields 10 may be initiated. The particular importance of the tab will be described in greater detail hereinbelow with respect to the use of the system 22.

Figure 5:
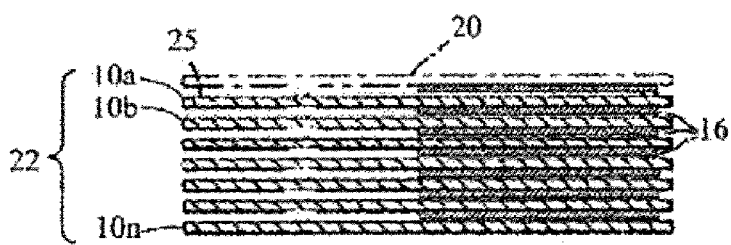
FIG. 5 is a cross-sectional view of the stethoscope shield system along line III-III of FIG. 3 in accordance with the present invention.

Adhesive bonding strength between the adhesive pad 16 of the lowermost shield 10*a* that contacts the instrument is preferably stronger than the adhesive bonding between the remaining successive shields 10 to aid in securely maintaining the system 22 with respect to the instrument as individual shields 10 are sequentially removed. Moreover, the adhesive bonding strength between each of the individual shields 10 from the lowermost shield 10*a* to the uppermost shield 10*n* progressively decreases to prevent groups of shields 10 from being unintentionally removed, thereby reducing waste of unused shields 10. Furthermore, the adhesive pad 16 disposed between the stacked shields may have a consecutively increasing bonding area and/or a consecutively increasing adhesive bonding strength along a direction toward the surface to which the system 22 is mounted. For example, as shown in FIGS. 4 and 5, the adhesive pads 16 increase in either bonding area or adhesive bonding strength from the uppermost shield 10*n* to the lowermost shield 10*a*. In addition, as detailed above, the adhesive pad 16 may be formed as a strip of adhesive material extending along a direction perpendicular to the extending direction of the tab 24 of the shield 10. Accordingly, the adhesive strip for each consecutive shield of the group of shields 10 from the lowermost shield 10*a* to the uppermost shield 10*n* may be disposed at an increasing distance away from the tab 24 toward the central region C. This consecutively staggering placement of the adhesive strip would prevent underlying shields 10*a*, 10*b* from being subjected to the pulling forces required to remove overlying used shields 10*n*.

The adhesive pads 16 are illustrated as being in a substantially semicircular pad having the diameter D slightly smaller than a diameter of the shield 10. In order to provide for decreased adhesive bonding from the lowermost shield 10*a* to the uppermost shield 10*n*, surface area of the adhesive pads 16 decreases from the lowermost shield 10*a* to the uppermost shield 10*n*. As seen in FIG. 4, the adhesive pad 16 between the release liner 20 and the lowermost shield 10*a* has a surface area greater than an adjacent adhesive pad 16 between the lowermost shield 10*a* and the next lowermost shield 10*b*. The surface areas of the adhesive pads 16 decrease from the lowermost shield 10*a* to the uppermost shield 10*n* such that a demarcation line of the adhesive pad 16 recedes away from the tab 24. As seen in FIGS. 2 and 4, the adhesive pads 16 from the lowermost shield 10*a* to the uppermost shield 10*n* may extend past central regions C of the shields 10 toward tab 24 by decreasing distances.

Alternatively, as seen in FIG. 5, in order to provide for decreasing adhesive bonding strengths from the lowermost shield 10*a* to the uppermost shield 10*n*, the surface areas of the adhesive pads 16 may remain substantially constant from the lowermost shield 10*a* to the uppermost shield 10*n* while different adhesives having different bonding strengths may be used. For example, the adhesive pad 16 corresponding to the lowermost shield 10*a* may have the highest bonding strength compared to bonding strengths of the adhesive pads 16 of the remaining shields 10 of the system 22.

Moreover, in order to provide for decreasing adhesive bonding strengths from the lowermost shield 10a to the uppermost shield 10n, combinations of different surface areas of the adhesive pads 16 and the use of different adhesives having different bonding strengths may be used. For example, the adhesive pad 16 formed on the lowermost shield 10a may have both the smallest surface area of other adhesive pads 16 corresponding to the other shields 10, but may be formed of an adhesive having the highest adhesive bonding strength. Similarly, the adhesive pad 16 formed on the uppermost shield 10n may have both the largest surface area of other adhesive pads 16 corresponding to the other shields 10, but may be formed of an adhesive having the lowest adhesive bonding strength. Moreover, the adhesive pads 16 corresponding to each of the shields 10 may be formed having different geometries in order to establish the range of increasing surface areas with which to be formed on the shields 10. For example, the geometry of the adhesive pad 16 corresponding to the lowermost shield 10a may encompass substantially a majority of the surface area of the lowermost shield 10a to ensure intimate, continuous contact with the instrument to which is attached/bonded to, whereas the geometry of the adhesive pad 16 corresponding to the uppermost shield 10n may encompass a relative minority of the surface are of the uppermost shield 10n. In order to encompass the relative minority, the geometry of the adhesive pad 16 corresponding to the uppermost shield 10n may comprise a thin line of adhesive placed along a portion of the circumference 18 of the uppermost shield 10n.

Figure 6:
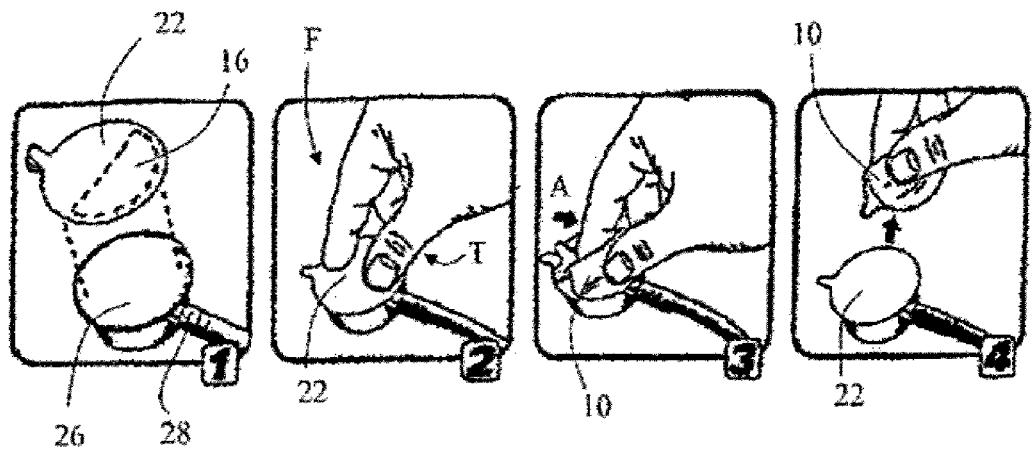
FIG. 6 is an illustration of an exemplary sequential method of using a stethoscope shield system in accordance with the present invention.

With reference now to FIG. 6, once the system 22 is removed from its packaging (not shown), the release liner 20 is removed from the uppermost shield 25 to expose the adhesive pad 16 of the initial shield 10 in the system 22. This stack is then secured to a diaphragm 26 of a stethoscope head 28. The stethoscope head 28 may take on numerous configurations with the particular configuration of the adhesive pad 16 applied to the shield 10 being optimally suited for the particular stethoscope head 28. Once again, this concept may be applied to any instrument wherein it is desired to shield a contaminant free surface of the instrument which is applied to the surface of successive patients. With the exposed adhesive pad 16, the stack of shields 10 is secured to the diaphragm 26 and maintained in the position with respect to the stethoscope head 28. In practice, the outermost shield 10 may become contaminated when applying the stack of shields 10 to the stethoscope head 28. In this regard, prior to application of the stethoscope to a patient, the initial shield 10 may be readily removed in the manner illustrated in FIG. 6. The initial shield 10 is grasped by the user by way of using the thumb T and forefinger F while the user exerts downward pressure with the forefinger F to frictionally engage the outermost shield 10 and the thumb T is held relatively stationary corresponding to the adhesive pad 16. Next, the user references the tab 24 with which to use a pinching motion using the forefinger F upon the surface of the outermost shield 10, thereby causing that portion of the inner surface of the outermost shield 10 lacking adhesive pad 16 to buckle from the underlying shield 10. Then, the outermost shield 10 is grasped and peeled off of the remaining underlying stack of shields 10. Accordingly, a fresh shield 10 is now exposed for the next patient. In addition, the buckled portion of the inner surface may now be attached to the adhesive pad 16 to facilitate disposal of the now-removed shield 10. Alternatively, as detailed above, a multilayered adhesive pad may be used for the adhesive pad 16, such that the now-removed shield 10 may be not be buckled and bonded together.

As noted hereinabove, the adhesive utilized in connection with the present invention is that similar to the adhesive in note pads sold by 3M Corporation under the trademark "Post-It Note". This adhesive is substantial enough to maintain the shields 10 in a stacked configuration with respect to one another, however, permits the exposed shield to be readily removed by using the pinching motion upon the shield 10 and peeling the exposed shield 10 away from the remaining plurality of shields 10 of the system 22. Further, the adhesive pad 16 of the initial shield 10 contacting the diaphragm 26 may be stronger than the adhesive pad 16 between the remaining successive shields 10 to aid in maintaining the system 22 secure with respect to the diaphragm 26 as shields 10 are sequentially removed.

As is known in the art, the stethoscope head 28 utilizes the diaphragm 26 in order to convert vibrations received from the skin of the patient into sounds which may be heard through ear pieces of the stethoscope (not shown). The system 22 is applied to the diaphragm 26 in a manner which permits the health care provider to continue to convert these vibrations received from the skin of the patient into sounds which can be heard by the health care provider. While FIG. 4 illustrates significant spacings provided between each of the shields 10 by the adhesive pad 16, the spaces in reality is minimal with FIG. 4 being an exaggeration of the adhesive pad 16 and shield 10 thickness. Additionally, the shields 10 are preferably of a diameter slightly greater than that of the stethoscope diaphragm 26 to prevent the edge of the diaphragm 26 from contacting the patient. However, the diameter of the initial shield 10 that is attached to the diaphragm 26 may be smaller than the diameter of the diaphragm 26, while still providing the greatest bonding strength of all of the subsequent adhesive pads 16 and shields 10 of the system 22.

As noted hereinabove, the plurality of shields 10 forming the system 22 are attached to the diaphragm 26 of the stethoscope 28 by a releasable adhesive so that the shield 10 covers the entire surface of the diaphragm 26. This is accomplished by adhesively attaching the system 22 directly to the diaphragm 26. The thickness of the adhesive pad 16 provided between the plurality of shields 10 is between about 0.01 mils to about 0.5 mils thick, and preferably within a range of about 0.1 mils to about 0.5 mils thick. Preferably, the adhesive pad 16 will be no more than that necessary to hold the shields together forming the system 22, as well as holding the system 22 to the stethoscope itself. In such a small amount, the adhesive 16 provides very little air space between the shields. Furthermore, because the adhesive pad 16 is preferably provided having a minimal thickness, the adhesive pad 16 does not act as a barrier to the conversion of vibrations received from the skin of the patient into sounds which are detected by the health care provider. Once the stethoscope 28 having the system 22 is formed, as illustrated in FIG. 6, the stethoscope 28 may be applied to a patient's body. Once the examination of the this initial patient is completed, the health care provider need merely perform the pinching motion upon the exposed shield 10 with reference to the tab 24 and remove the shield 10 from the system 22, thus exposing the new shield 10 underlying the removed shield 10. The stethoscope 28 can then be utilized on a subsequent patient without fear of contamination, thus minimizing the transfer of microorganisms or other contaminants from one patient to the other.

It should further be noted that while the foregoing discussion sets forth an adhesive being used to secure the shields to one another, the adhesion may be realized by using electrostatic forces or heat seals between the shields. Moreover, ultrasonic and pressure bonding may be used to bond the shields together. This is particularly useful if the shields are of a plastic material. An adhesive may be used to secure the entire stack to the stethoscope.

As can be seen from the foregoing, the present invention provides a system which permits the health care provider to readily perform numerous observations of patients, one after the other, while ensuring that a non-contaminated application surface is provided. The health care provider need not locate remote individual shields provided in the patient's room or elsewhere, but merely remove an exposed shield from a system of shields which are already applied to the stethoscope. Once the system has been depleted, the health care provider need merely apply a subsequent system to the stethoscope head and continue the examination of patients. Accordingly, the transfer of microorganisms and other contaminants from patient to patient is minimized in an efficient manner in accordance with the present invention.

While the present invention has been described in reference to preferred embodiments, it will be appreciated by those skilled in the art that the invention may be practiced otherwise than as specifically described herein without departing from the spirit and scope of the invention. It is, therefore, to be understood that the spirit and scope of the invention be only limited by the appended claims.

What is claimed is:

1. A shield system for an instrument having a surface area for touching a body of a person, the system comprising:
    a plurality of substantially planar shields, each having a substantially identical outer periphery, stacked one upon the other with an adhesive disposed therebetween, each of said shields further including a first surface and a second surface with said first surface of each of said shields adhering to said second surface of an adjacent shield by said adhesive; and
    a first shield of said stacked shields being adhered to said surface area of said instrument for supporting said stacked shields;
    wherein said adhesive disposed between said stacked shields covers less than an entire surface of at least one of said first and second surfaces and has at least one of a consecutively increasing bonding area and a consecutively increasing bonding strength between each successive shield of said stacked shields, and an exposed shield of said stacked shields is removed after contacting the body.

2. The system as defined in claim 1, wherein the instrument is a stethoscope and the surface is a diaphragm of the stethoscope.

3. The system as defined in claim 1, wherein each of said shields includes at least one of a tab extending from a periphery of said shield and an indicator mark at a periphery of said shield.

4. The system as defined in claim 3, wherein said adhesive is applied to a selective region of said first surface of said shields at a position opposite to one of said tab and said indicator mark.

5. The system as defined in claim 4, wherein said adhesive is applied adjacent a periphery of said first surface of said stacked shields.

6. The system as defined in claim 5, wherein a central region of said first surface of said stacked shields includes said adhesive.

7. The system as defined in claim 1, wherein a thickness of each of said shields is in a range of about 0.10 to about 4.0 mils.

8. The system as defined in claim 1, wherein each of said shields is formed of a material which is not readily permeable by at least one of liquids and microbes.

9. A method for preventing contamination of an instrument surface of an instrument comprising the steps of:
    applying a plurality of substantially planar shields, each having a substantially identical outer periphery, stacked one upon the other with an adhesive disposed therebetween to a surface of said instrument, each of said shields further including a first surface and a second surface such that adjacent shields adhere to one another with said first surface of each of said shields adhering to said second surface of an adjacent shield and said first surface of a first shield in said stacked shields adjacent to said instrument surface is adhered to said instrument surface by said adhesive; and
    removing an outermost shield of said stacked shields after said instrument has been used,
    wherein said adhesive disposed between said stacked shields covers less than an entire surface of at least one of said first and second surfaces and has at least one of a consecutively increasing bonding area and a consecutively increasing bonding strength between each successive shield of said stacked shields.

10. The method as defined in claim 9, wherein said instrument is a stethoscope and said surface is a diaphragm of said stethoscope.

11. The method as defined in claim 10, wherein each of said shields includes at least one of a tab extending from a periphery of said shield and an indicator mark at a periphery of said shield.

12. The method as defined in claim 10, wherein said first shield includes a fenestrated structure.

13. The method as defined in claim 10, wherein said adhesive is applied to said first surface of each of said stacked shields.

14. The method as defined in claim 13, further comprising a step of removing a release liner from said stacked shields to adhered said stacked shields to said surface of said diaphragm prior to applying said stacked shields to said surface of said diaphragm.

15. The method as defined in claim 13, wherein said adhesive is applied to selective regions of said first surface.

16. The method as defined in claim 15, wherein said adhesive is applied adjacent a periphery of said first surface.

17. The method as defined in claim 16, wherein a central region of said first surface includes said adhesive.

18. The method as defined in claim 9, wherein a thickness of each of said shields is in a range of 0.10 to 4.0 mils.

19. The method as defined in claim 9, wherein each of said shields is formed of a material which is not readily permeable by at least one of liquid and microbes.

20. The method as defined in claim 9, wherein the step of removing an outermost shield of said stacked shields includes a pinching movement of said outermost shield to buckle said outermost shield.

21. The method as defined in claim 20, wherein said pinching movement is aligned along a direction opposite to at least one of a tab extending from a periphery of said shield and an indicator mark at a periphery of said shield.

22. A shield system for application to a contact surface of an instrument comprising:
    a plurality of substantially planar shields, each having a substantially identical outer periphery, stacked one upon the other, each of said shields including a first surface and a second surface such that adjacent shields are attracted to one another with said first surface of each of said shields contacting said second surface of an adjacent shield; and a first shield of said stacked shields being in contact with the instrument for supporting said stacked shields, wherein said attraction between said stacked shields occurs over less than an entire surface of at least one of said first and second surfaces and has at least one of a consecutively increasing attraction area and a consecutively increasing attraction strength between each successive shield of said stacked shields, and an exposed shield of said stacked shields is removed after contacting a body.

23. The shield system as defined in claim 22, wherein said attraction occurs at selected regions of said first surface of said stacked shields.

24. The shield system as defined in claim 23, wherein said attraction occurs adjacent a periphery of said first surface of said stacked shields.

25. The shield system as defined in claim 23, wherein said attraction occurs at a central region of said first surface of said stacked shields includes said adhesive.

26. The shield system as defined in claim 22, wherein a thickness of each of said shields is in a range of 0.10 to 4.0 mils.

27. The shield system as defined in claim 22, wherein each of said shields is formed of a material which is not readily permeable by at least one of liquid and microbes.

28. The shield system as defined in claim 23, wherein each of said shields includes at least one of a tab extending from a periphery of said shield and an indicator mark at a periphery of said shield, and said selected region of said first surface of said stacked shields is at a position opposite one of said tab and said indicator mark.

29. The shield system of claim 22, wherein said planar shields are attracted to one another by at least one of thermal bonding, pressure bonding and ultrasonic welding.

30. A stethoscope shield system for a stethoscope having a diaphragm with a surface area for touching a body of a person, the system comprising:

a plurality of substantially planar shields, each having a substantially identical outer periphery, stacked one upon the other, each of said shields including a first surface and a second surface with said first surface of each of said shields being attracted to said second surface of said adjacent shield by an attraction force; and a first shield of said plurality of shields being in contact with said diaphragm for supporting said stacked shields, wherein said attraction force between said stacked shields occurs over less than an entire surface of at least one of said first and second surfaces and has at least one of a consecutively increasing attraction force area and a consecutively increasing attraction force strength between each successive shield of said stacked shields, and an exposed shield of said stacked shields is removed after contacting said body.

31. The shield system of claim 30, wherein said planar shields are attracted to one another by at least one of thermal bonding, pressure bonding and ultrasonic welding.

32. The system as defined in claim 30, further comprising a release liner devoid of said adhesive positioned adjacent said first shield, said release liner being removed prior to adhering said first shield to said diaphragm.

33. The system as defined in claim 32, wherein said first shield includes a fenestrated structure.

\* \* \* \* \*